US008473314B2

(12) United States Patent
Patton et al.

(10) Patent No.: US 8,473,314 B2
(45) Date of Patent: Jun. 25, 2013

(54) METHOD AND SYSTEM FOR DETERMINING PRECURSORS OF HEALTH ABNORMALITIES FROM PROCESSING MEDICAL RECORDS

(75) Inventors: Robert M. Patton, Knoxville, TN (US); Thomas E. Potok, Oak Ridge, TN (US); Barbara G. Beckerman, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 259 days.

(21) Appl. No.: 13/033,756

(22) Filed: Feb. 24, 2011

(65) Prior Publication Data
US 2011/0218823 A1    Sep. 8, 2011

Related U.S. Application Data

(60) Provisional application No. 61/310,351, filed on Mar. 4, 2010, provisional application No. 61/331,941, filed on May 6, 2010.

(51) Int. Cl.
*G06F 19/00* (2011.01)
(52) U.S. Cl.
USPC .................................................. 705/3
(58) Field of Classification Search
USPC .............................. 705/3; 725/18
See application file for complete search history.

(56) References Cited

U.S. PATENT DOCUMENTS

2005/0044561 A1*  2/2005  McDonald ...................... 725/18

OTHER PUBLICATIONS

Patton, Robert M., et al., "Analysis of Mammography Reports Using Maximum Variation Sampling," Oak Ridge National Laboratory, GECCO'08, Jul. 12-16, 2008, Atlanta, Georgia, USA, 4 pages.
Patton, Robert M., et al., "A Genetic Algorithm for Learning Significant Phrase Patterns in Radiology Reports," Oak Ridge National Laboratory, GECCO'09, Jul. 8-21, 2009, Montreal, Quebec, Canada, 6 pages.

* cited by examiner

*Primary Examiner* — John Pauls
(74) *Attorney, Agent, or Firm* — Boyle Fredrickson, S.C.

(57) ABSTRACT

Medical reports are converted to document vectors in computing apparatus and sampled by applying a maximum variation sampling function including a fitness function to the document vectors to reduce a number of medical records being processed and to increase the diversity of the medical records being processed. Linguistic phrases are extracted from the medical records and converted to s-grams. A Haar wavelet function is applied to the s-grams over the preselected time interval; and the coefficient results of the Haar wavelet function are examined for patterns representing the likelihood of health abnormalities. This confirms certain s-grams as precursors of the health abnormality and a parameter can be calculated in relation to the occurrence of such a health abnormality.

18 Claims, 4 Drawing Sheets

TABLE 3. TOP THREE PRECURSOR S-GRAMS

| S-GRAM | OCCURRENCES AS PRECURSOR | OCCURRENCES IN SELECTED PATIENTS | PER CENT OCCURRENCES AS PRECURSOR |
|---|---|---|---|
| LYMPH & NODE | 39 | 71 | 54.93 % |
| CM & DENSITY | 12 | 24 | 50.00 % |
| NODULAR & DENSITY | 51 | 104 | 59.04 % |

Fig. 3

TABLE 4. PRECURSOR LEAD TIME

| S-GRAM | AVE. TIME ELAPSED (YRS.) | STD. DEV. (YRS.) | SKEWNESS/ KURTOSIS |
|---|---|---|---|
| LYMPH & NODE | 4.2 | 2.9 | 0.01/-1.38 |
| CM & DENSITY | 1.1 | 2.2 | 2.63/6.91 |
| NODULAR & DENSITY | 2.9 | 2.9 | 0.68/-0.64 |

Fig. 4

TABLE 5. % INCREASE IN FREQUENCY

| S-GRAM | PER CENT OCCURRENCES IN ALL PATIENTS | PER CENT OCCURRENCES IN SELECTED PATIENTS | PER CENT INCREASE OCCURRENCES |
|---|---|---|---|
| LYMPH & NODE | 25.17 | 57.72 | 129.34 % |
| CM & DENSITY | 5.50 | 19.51 | 254.51% |
| NODULAR & DENSITY | 31.39 | 84.55 | 169.35% |

METHOD AND SYSTEM FOR DETERMINING PRECURSORS OF HEALTH ABNORMALITIES FROM PROCESSING MEDICAL RECORDS

CROSS REFERENCE TO RELATED APPLICATIONS

The benefit of priority based on U.S. Prov. Appl. No. 61/310,351, filed Mar. 4, 2010 and U.S. Prov. Appl. No. 61/331,941, filed May 6, 2010 is claimed herein.

STATEMENT REGARDING FEDERALLY SPONSORED RESEARCH

This invention was made with assistance under Contract No. DE-AC05-00OR22725 with the U.S. Department of Energy. The Government has certain rights in this invention.

BACKGROUND OF THE INVENTION

The field of the invention is computer methods for determining precursors of health abnormalities from processing patient medical records.

In mammography, much effort has been expended to characterize findings in the radiology reports prepared by doctors of radiology. Various computer-assisted technologies have been developed to assist radiologists in detecting cancer; however, the algorithms still lack high degrees of sensitivity and specificity, and must undergo machine learning against a training set with known pathologies in order to further refine the algorithms with higher validity of truth. In a large database of reports and corresponding images, automated tools are needed just to determine which data to include in the training set. Radiologists disagree with each other over the characteristics and features of what constitutes a normal mammogram and the terminology to use in the associated radiology report. Abnormal reports follow the lexicon established by the American College of Radiology Breast Imaging Reporting and Data System (Bi-RADS), but even within these reports, there is a high degree of text variability and interpretation of semantics. The focus has been on classifying abnormal or suspicious reports, but even this process needs further layers of clustering and gradation, so that individual lesions can be more effectively classified.

The knowledge to be gained by extracting and integrating meaningful information from radiology reports will have a far reaching benefit, in terms of the refinement of the classifications of various findings within the reports. In the near-term, the overall goal of k is to accurately identify abnormalities reported in radiology reports amid a massive collection of reports. The challenge in achieving this goal lies in the use of natural language to describe the patient's condition.

Therefore, an automated method is needed for learning the characteristic cue phrase patterns of the natural language used in the radiology reports and using those learned patterns as a basis for automatically categorizing, clustering, or retrieving relevant data for the user.

In the paper entitled "Analysis of Mammography Reports using Maximum Variation Sampling," Patton, R. M; Beckerman, B., and Potok, T. E. presented at 4th GEECO Workshop on Medical Applications of Genetic and Evolutionary Computation (MedGEC) Atlanta, Ga. July, 2008, ACM Press, New York, N.Y. 2061-2064, the maximum variation sampling algorithm (MVSA) for analyzing radiological medical reports was described.

In a test data set, the data set comprised approximately 120,000 reports. Within this data are numerous reports that simply stated that the patient canceled their appointment. These reports are very small in length and are exceptionally distinct from all other reports (similarity values approaching zero). Unfortunately, the MVSA as proposed there gravitated toward these cancellation reports as the best solution for a maximum variation sample. In an effort to effectively characterize the phrase patterns of the mammography reports, it is necessary to examine reports that are longer in length, so that more language can be examined for patterns. In addition, abnormal reports tend to be longer in length than normal reports since the radiologist is describing the abnormalities in more detail. Consequently, the MVSA in this paper needed to be improved upon.

Other techniques of reducing the number of reports and better evaluating their significance over time were also sought after.

SUMMARY OF THE INVENTION

The present invention provides an improved method and system for processing data in medical records using a computing apparatus for determining a parameter of a health abnormality precursor.

In one aspect, the method is improved by applying a Haar wavelet function to the s-grams from the fitness-reduced MVSA sample of medical records over the preselected time interval, and by reducing the number of medical records for reporting by analyzing coefficient results from applying the Haar wavelet function.

The reduced number of medical records can them be processed to generate a report with at least one parameter representing a health abnormality precursor through a computing output device to a human observer. Several examples of such parameter will be described below. The parameters can be displayed on a screen of a computer or communicated to a human through any one of various well known computer output devices for communicating this information.

In a further aspect, the method is improved by applying one or more fitness functions to the results of the initial MVSA, to reduce a number of medical records being processed and to increase the diversity of the medical records being processed.

Other objects and advantages of the invention, besides those discussed above, will be apparent to those of ordinary skill in the art from the description of the preferred embodiments, which follows. In the description reference is made to the accompanying drawings, which form a part hereof, and which illustrate examples of the invention. Such examples, however, are not exhaustive of the various embodiments of the invention, and therefore reference is made to the claims, which follow the description for determining the scope of the invention.

DETAILED DESCRIPTION OF THE PREFERRED EMBODIMENTS

In this example, reports from 12,809 patients from a 5-year period were analyzed. There were 61,064 actual reports in this set, which include a number of reports that simply stated that the patient canceled their appointment. The focus in this study involved studying the patients with multiple reports over time. Some of these patients have reports that predate the five-year time period and also have diagnostic screenings, indicating a potential health problem. Abnormal reports tend to have a richer, broader, and more variable vocabulary than normal reports. In addition, normal reports tend to have a higher number of "negation" phrases. These are phrases that begin with the word "no" such as the phrase "no findings suggestive of malignancy". Another challenge in analyzing the natural language of these reports is that there are multiple ways of conveying the same meaning. Phrases such as "no strongly suspicious masses" and "no new suspicious mass lesions" both mean that nothing health abnormality was observed. To account for this variability in the language, we used the natural language processing technique known as skip bigrams, or s-grams. S-grams are word pairs in their respective sentence order that allow for arbitrary gaps between the words. For example, the s-gram for the previous phrase examples is the words no and suspicious. As known in the art, s-grams are an elective technique in determining normal and abnormal reports. The next step is to analyze patient records to determine if abnormal report occurrences can be forecasted.

Our objective was to identify whether certain phrase patterns exist within patient reports that act as precursors to future abnormalities. To explore this, we analyzed the patient records that contain a higher number of reports. This narrowed the patient data set to 667 patients who had between twelve (12) and sixteen (16) reports each. Of these patients, the ones of most interest for this work are those with discernable patterns in their medical reports. For example, a patient with cancer may have had an early report that mentions something unusual or suspicious, followed by years of normal reports, before the cancer appeared. The early report may be a precursor for the cancer. To identify these patients, each report in each patient record is analyzed to count the number of normal and abnormal s-grams. This provided a temporal sequence of normal and abnormal s-gram counts for each patient record. The following table shows an example patient record where s-grams were counted for each report.

Figure 1:
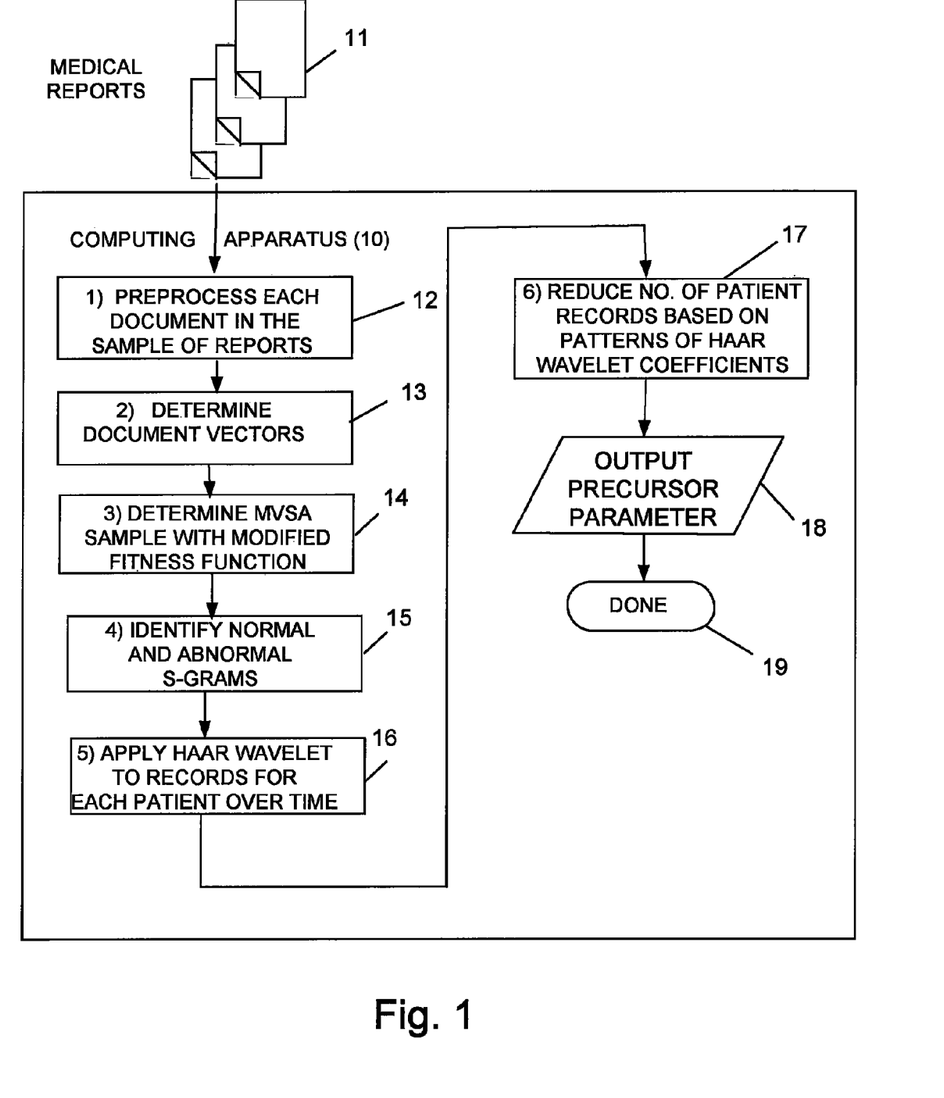
FIGS. 1-2 are flow charts of a method and computer program for practicing a detailed embodiment of the present invention.

Referring to FIG. 1, the method of the present invention was applied to the number of medical reports represented by symbols 11, which are input into a computing apparatus 10. The documents 11 are either text-recognizable or are converted to that form using an optical character recognition program routine. The documents 11 are first preprocessed according to a known document processing technique illustrated in more detail in FIG. 2. In the computing methods illustrated in FIGS. 1 and 2, the blocks represent groups of program instructions which are part of a computer program executed in the computing apparatus 10.

The computing apparatus may be a PC or Apple Mac personal computer of a type known in the art. The PC or Mac computer must include a Java application program 1.6, as the program instructions are preferably authored in the JAVA programming language. The computer should have a minimum of 512 MB of RAM. The operation system can be any one of Windows, Linux, or Mac so long as Java 1.6 runs on that OS.

Figure 2:
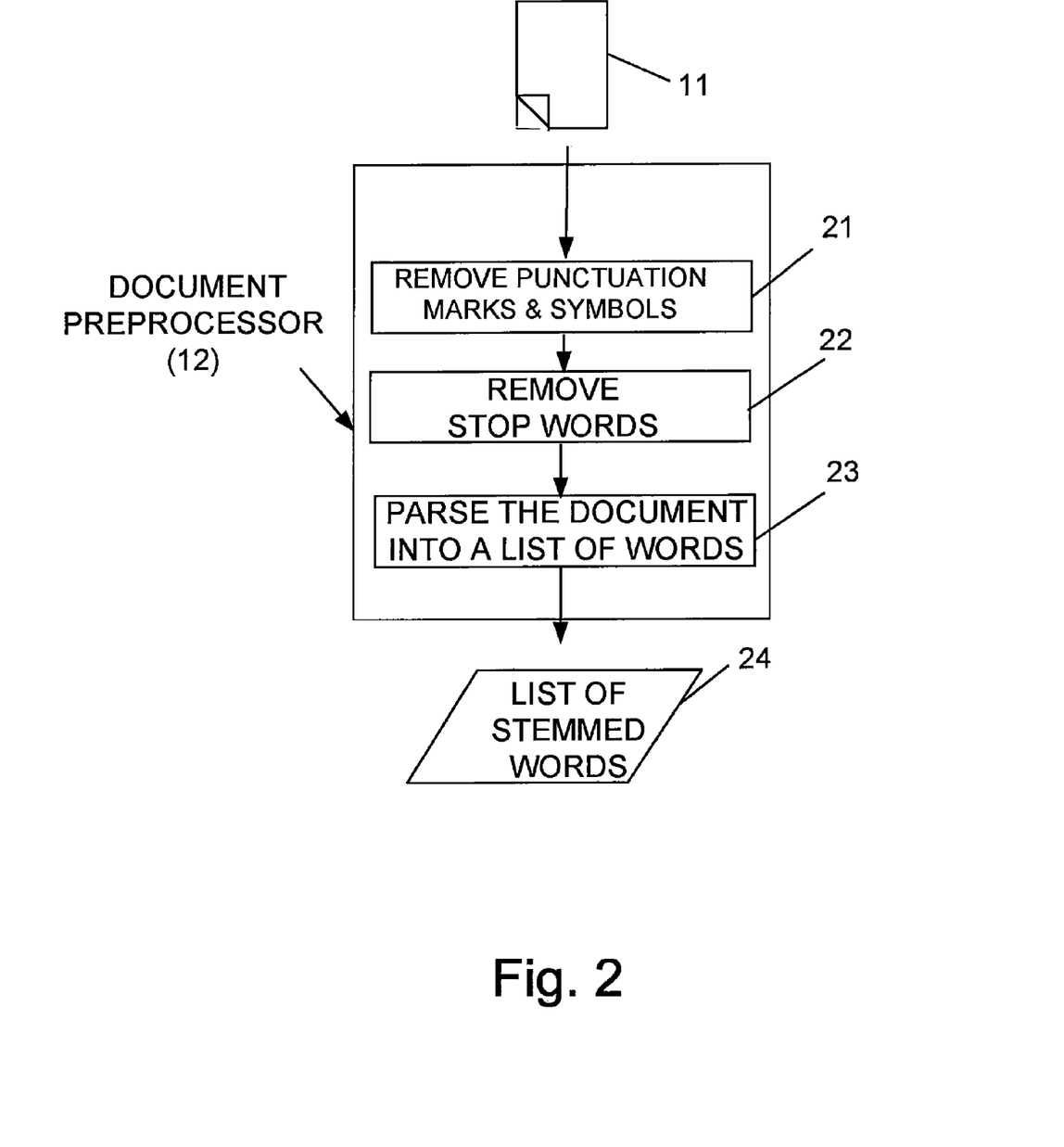

Referring to FIG. 2, documents are processed by removing punctuation marks and symbols as represented by process block 21 in FIG. 2. Next, stop words are removed as represented by process block 22 in FIG. 2 and the document is parsed into a list of words using a Porter stemming algorithm as represented by process block 23. The list of stemmed words is an output of this routine, as represented by I/O block 24.

Returning to FIG. 1, the medical reports are then converted to documents vectors as represented by process block 13. In this form, a frequency vector of word and phrase occurrences within each document can represent each document. Once document vectors models have been produced, a maximum variation sampling algorithm (MVSA) can be applied as represented by process block 14.

Two components of implementing the algorithm are the encoding of the problem domain into the document population and applying the fitness function to be used for evaluating individuals in the population. To encode the data, each individual document is selected from a population of documents N over a preselected time interval. Each individual consists of N documents where each item represents one document (each document is given a unique numeric identifier) in the sample. For example, if the sample size were 30, each item in the sample would represent a medical record of one patient visit or one medical test result. The records could pertain to one patient over a time interval or to several patients over the time interval.

To measure the variation (or diversity) of our samples, the summation of the similarity between the vector-space models of each document in the sample is calculated as shown in the following equations. In this equation, the Similarity function calculates the distance between the document vectors of document j and k of the individual patient i. This distance value ranges between 0 and 1 with 1 meaning that the two documents are identical and 0 meaning they are completely different in terms of the words used in that document. Therefore, in order to find a sample with the maximum variation.

$$\text{Fitness}(i) = \sum_{j=0}^{N} \sum_{k=j+1}^{N} \alpha_j + \beta k + \text{Similarity}(vect(i, j), vect(i, k)) \quad \text{Equation (1)}$$

The similarity equation is converted to a fitness function by limiting the documents to be judged for similarity according to the following measures in Equations (2) and (3):

$$\alpha_j = e^{-\left(\frac{\|j\|}{100}\right)} \quad \text{Equation (2)}$$

$$\beta_k = e^{-\left(\frac{\|k\|}{100}\right)} \quad \text{Equation (3)}$$

Equation 1 must be minimized (i.e., lower fitness values are better). In this fitness function, there will be $(N^2-N)/2$ comparisons for each sample to be evaluated.

The functions of equations (2) and (3) are incorporated into the MVSA function of equation (1) to reduce the influence of documents in the maximum variation sampling based on the length of the documents. Shorter documents are weighted less important while longer documents are weighted more important. These functions return values that are between 0 and 1, inclusive.

After the MSVA is executed, as represented by process block 14, the end result is a best sample of documents that are as diverse from each other as possible. Once this sample is achieved, then phrases are extracted from each document in the sample. For each phrase in the document, normal and abnormal s-grams are extracted as represented by process block 15. Next, the s-grams are counted across the sample of documents. S-grams that are common across the sample will have higher frequency counts while s-grams with a frequency of 1 will uniquely identify a particular document in the sample. Only those s-grams that are the most common in the best sample found are considered significant.

The MVSA is augmented with a memory for learning the common s-grams of the failed individuals. This will enable answering questions such as what characteristic phrases make failed individuals inferior to successful individuals. After each generation, s-grams and their frequencies from each failed individual are extracted from each individual and stored in a memory in the computing apparatus 10. After the MVSA has completed, the memory now contains the most common abnormal s-grams, which are identified by executing instructions represented by process block 15 in FIG. 1.

In the example shown in Table 1 below, there is some abnormality that is mentioned in an early record (May 24, 1984) and then the record contains multiple abnormal s-grams toward the latest records (beginning on Dec. 7, 1991). The normal and abnormal s-gram counts form a temporal sequence for each patient. The method described herein is designed to be able to compare patients based on these sequences.

TABLE 1

Example of Normal and Abnormal S-grams for Patient A

| Date of Test Record | Normal S-Grams | Abnormal S-Grams |
|---|---|---|
| May 20, 1981 | 1 | 0 |
| May 24, 1984 | 3 | 1 |
| Jun. 3, 1985 | 3 | 0 |
| Mar. 9, 1988 | 1 | 0 |
| Jul. 12, 1989 | 4 | 0 |
| Dec. 5, 1990 | 3 | 0 |
| Dec. 7, 1991 | 1 | 4 |
| Mar. 11, 1992 | 0 | 4 |
| Mar. 11, 1992 | 0 | 4 |
| Mar. 22, 1992 | 0 | 1 |
| Mar. 22, 1992 | 0 | 1 |
| Mar. 23, 1992 | 0 | 0 |
| Nov. 9, 1992 | 0 | 0 |

To find patients with similar patterns in the set of 667, a discrete Haar wavelet transform (DWT) is used to provide a temporal sequence of abnormal s-gram counts. A wavelet transform is a mathematical function that is used to split a function into separate scale components, thus providing a multi-resolution analysis. The wavelet transform is analogous to a prism that breaks light into its various spectral colors. Applying the DWT will identify the frequencies that constitute a temporal sequence, and will also identify the location in time in which those frequencies occur DWT further provides the ability for matching patterns despite amplitude and time shifts. In this method, a pattern-based approach is used, to find similar temporal patterns using DWT that does not rely on the use of thresholds. This enables a wider range of temporal patterns to be found that contain the basic temporal characteristics of interest. Each patient record consisted of 16 or fewer reports. For records with less than 16 reports, the temporal sequences were padded with zeros until there were 16 elements. Next, for each patient record, the temporal sequence of abnormal s-gram counts were transformed using a Haar wavelet, as represented by process block 16 in FIG. 1.

For example, the transform for patient A (of Table 1) is shown in the following Table 2.

TABLE 2

Haar Wavelet Transform of Abnormal S-gram Sequence for Patient A

| 1$^{st}$ Coefficient | 0.0375 | | | | | | | |
|---|---|---|---|---|---|---|---|---|
| Band 0 | 0.1875 | | | | | | | |
| Band 1 | −0.875 | 0.75 | | | | | | |
| Band 2 | 0.25 | −2 | 1 | 0 | | | | |
| Band 3 | −0.5 | 0 | 0 | 0 | 1.5 | 0.5 | 0 | 0 |

After each of the 667 patient records is transformed via a Haar wavelet, the next step is to begin looking for the patterns of interest, early abnormality and late anomaly and reduce the number of patient records, as represented by process block 17 in FIG. 1.

First, the resolution 1 of each patient is examined. Specifically, the first coefficient of resolution 1 (Band 1 in Table 2 above) should be less than 0 while the second coefficient of resolution 1 should be greater than 0. This particular pattern identifies those patients with an increasing amplitude change in their s-gram counts toward the end of the records (rather than at the beginning of their records), which suggests that diagnostic screening was performed near the end of the patient's record. Second, if the pattern for resolution 1 exists, then resolution 2 of each patient is examined. Specifically, either the first or second coefficient (or both) of resolution 2 (Band 2 in Table 2 above) should be less than 0 while the third and fourth coefficients should both be greater than 0. This particular pattern identifies those patients who have a short duration of abnormal s-gram counts early in the records, which suggests that some unusual feature about the patient was mentioned early in their record. For higher resolution, resolution 3 (Band 3 in Table 2 above) could be used instead of resolution 2. In that case, the first four coefficients would be checked for negative values, while the last four coefficients would need to be positive. Patient records that match these patterns in the Haar DWT are then selected. This reduced the data set to 123 patient records, which is approximately 1% of the original data set. For these selected patient records, all s-grams were extracted from the first report in which the abnormal s-gram count was at least 1 but less than or equal to the normal s-gram count. This represents a normal report where some potential abnormality was mentioned. Next, the time elapsed was computed between this first report and the next report where the abnormal s-gram count was higher than the normal s-gram count. This second report represents an abnormality that was detected and a diagnostic screening was requested. From the example data shown of patient A in Table 1, the first report would be the one dated May 24, 1984 and the next report would be the one dated Dec 7, 1991. All s-grams from the report dated May 24, 1984 are extracted and considered as potential precursor patterns. Finally, the frequency of each extracted s-gram was computed along with the corresponding average elapsed time. The results of this approach applied to the 123 selected patients are shown in the following tables and figures, each of which or all of which are outputs that can be selected, as represented by I/O block 18 in FIG. 1. A cycle of the process is then complete and represented by the done block 19.

Figure 3:
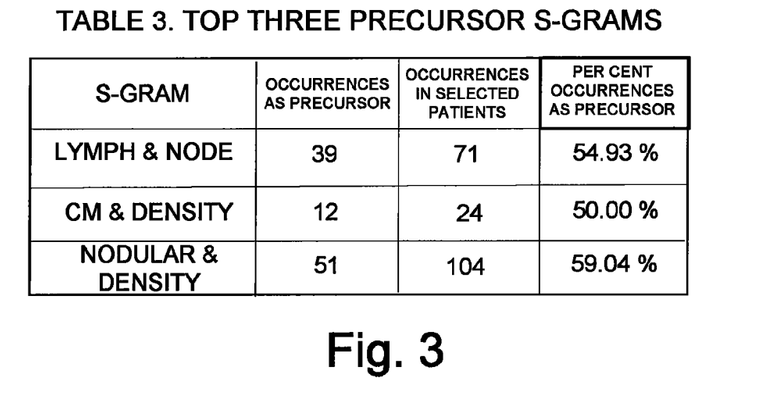
FIGS. 3-5 are tables of data seen on the screen of the computing apparatus of FIG. 4.

Table 3 in FIG. 3 shows the top three precursor s-grams that were observed, and these are labeled, "lymph and node," "centimeter (CM) and density" and "modular and density." In reviewing this table, there is no single definitive precursor s-gram. However, the top three s-grams have approximately a fifty percent occurrence as a precursor (column 3). This means that, of the 123 selected patients, if one of those s-grams were mentioned in the patient's record, then there is a fifty percent chance that the patient will have a diagnostic screening (i.e., an abnormality will be seen that requires additional testing) at some point in the future. While this percentage is equivalent to random selection, in comparison to the other s-grams found, these s-grams show promise as potential precursors and demonstrate a capability far beyond the current state of the practice, which is dependent entirely on manual analysis.

Figure 4:
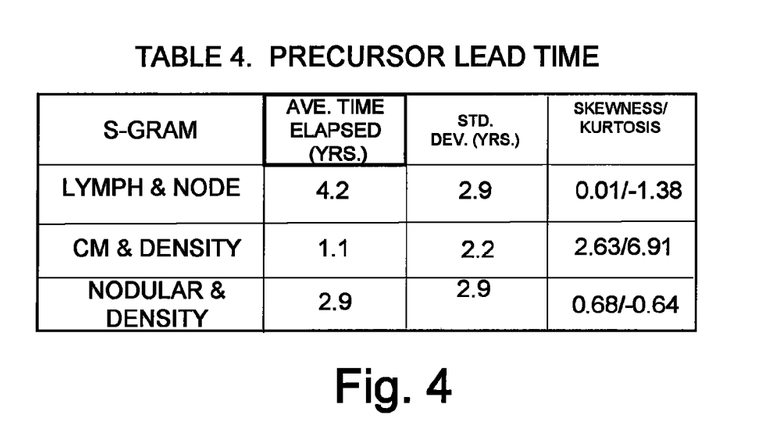

Table 4 in FIG. 4 shows the average elapsed time in units of days for each of the s-grams shown in Table 3. The first and third s-grams provide approximately a three-year to five-year lead-time. This provides a very early warning indication of a future abnormality. The drawback, however, is that the skewness and kurtosis values for these s-grams indicate significant variability in this window. The reason for this is that these terms are general and vague in their meaning, but still provide some level of indication that the radiologist sees a feature of concern. In contrast, the second s-gram (cm & density) provides a much more specific window with an average of just over one year with very high positive skewness and kurtosis values. The reason for this is that this s-gram represents phrase patterns that are very specific about a particular feature that was observed in the patient. An example phrase that this s-gram would represent is "2.5 cm area of asymmetric density". Such specificity by the radiologist suggests that the radiologist is very focused on this feature and is likely to be concerned enough to request additional diagnostic screenings. Consequently, the average time elapsed for this s-gram is much shorter and has less variability.

Figure 5:
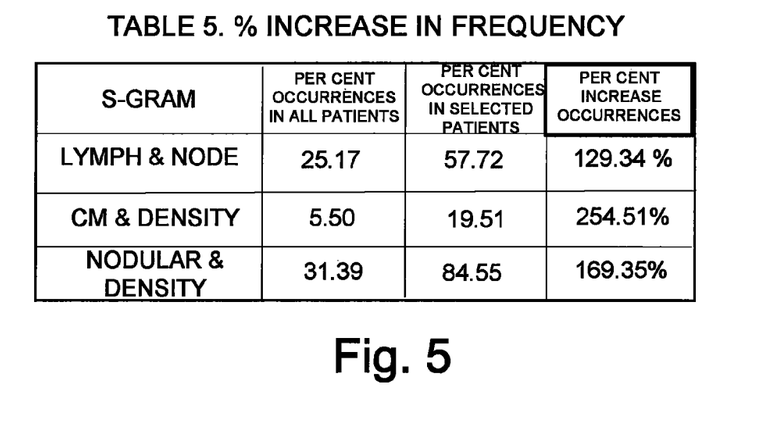

As seen in FIG. 5, the data in Table 5 shows the usage of frequency of the s-grams shown in Table 3. In document text analysis, terms and phrases that are commonly used in a document set are not considered useful in characterizing the content of a particular document. However, if a term or phrase is not commonly used in a document set and a particular document has a high frequency of that term or phrase, then it is considered significant to that document. In a similar manner, the frequencies of s-grams in Table 3 were computed over all of the patients (12,809 patients) and over the patients that were selected for analysis (123 patients). These frequencies, as well as the corresponding percent increase, are shown in Table 5, which again confirms the s-grams as being precursors. As can be seen, most of the s-grams have percent increases well over 100%. This is encouraging as it shows that these s-grams are highly related to patients with abnormalities. If the percent increases had been much below 100%, then this would indicate that these s-grams are very common, and consequently, the value as a precursor would be diminished. However, the percent increases and corresponding percent occurrence in selected patients shown in the table suggest that these s-grams have high potential as precursors.

Figure 6:
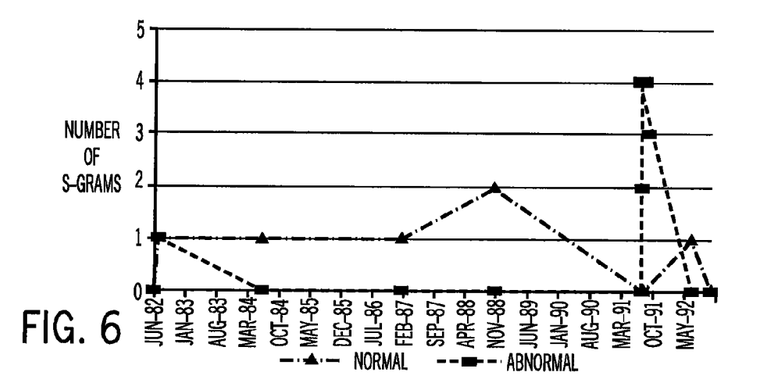
FIGS. 6-8 are graphs of data which can be displayed on the screen of the computing apparatus to illustrate the precursor status of reports for an individual patient.
Figure 7:
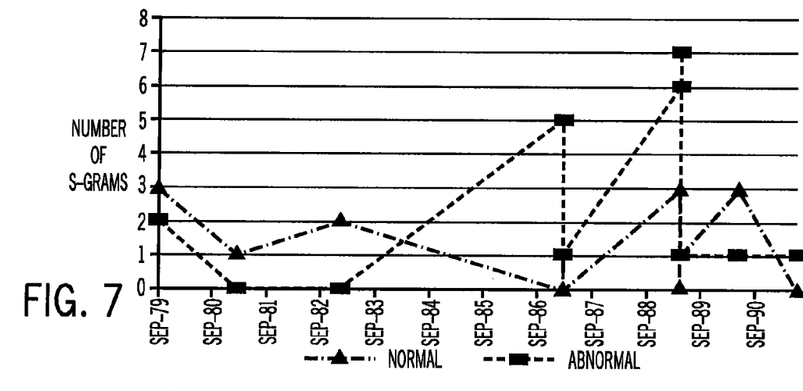
Figure 8:
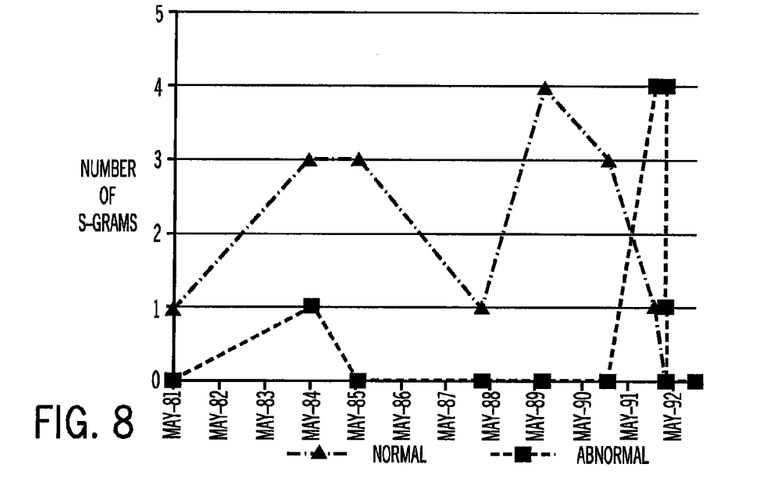

The figures show various patient records that were found using the approach described here. FIG. 6 shows the normal and abnormal s-gram counts of a patient record found by this approach where "lymph & node" was a precursor s-gram. In one of the first reports in this record, a radiologist made particular note of specific lymph nodes in this patient. This patient was ultimately diagnosed with grade 1 infiltrating ductal carcinoma (i.e., breast cancer) with tubular differentiation. FIG. 7 shows the normal and abnormal s-gram counts of another patient record found by this approach where "cm & density" was a precursor s-gram. In the first report of this record, the radiologist states "There is a less than 1 cm area of focal increased density seen only on the left craniocaudal view in the lateral aspect of the left breast." This patient was ultimately diagnosed with "mild fibrocystic disease with radial scar and focal florid sclerosing adenosis" in the right breast. FIG. 8 shows the normal and abnormal s-gram counts of another patient record found by this approach where "nodular & density" was a precursor s-gram. In one of the first reports, the radiologist states "There is prominent nodular density posteriorly and inferiorly in both breasts on the mediolateral oblique views, left more than right." This patient is ultimately diagnosed with a simple cyst. In that report, the radiologist states "Ultrasound directed to the inferocentral left breast 6 o'clock position demonstrates a 1-cm round, simple cyst." In each of these examples, it should be noted that the precursor s-gram does not necessarily provide specific information concerning the abnormality that is ultimately diagnosed. In the first two examples, the s-grams are not related to the ultimate diagnosis. In the third example, the precursor s-gram is related, but it cannot be conclusively determined that it is, in fact, the exact same abnormality that is ultimately diagnosed. However, what the precursor s-gram does provide is an early warning indication that the radiologist noted some feature about the patient that seemed unusual, or was noteworthy. The approach described here seeks to leverage that information, even if it does not ultimately relate to the final diagnosis.

The objective of our work was to answer the following questions:

"Do certain phrase patterns exist that act as precursors to future abnormalities in a patient?

"If so, how far in advance of the abnormality do they occur?"

As can be seen in the results, phrase patterns do exist that act as precursors. In addition, these precursors also hold the potential of providing lead times measured in years. This is potentially very significant, although additional work is needed to investigate this possibility. In this work, there are several other positive outcomes. First, in the approach developed, abnormal reports are identified based on s-grams related to diagnostic screenings, not based on specific types of abnormalities. Consequently, the precursor s-grams provide a general warning indication. Any form of early warning detection will provide various levels of specificity. This preliminary work provides the initial level of warning. Second, the results show that the precursor s-grams are used much more frequently in patients with abnormalities in comparison to the entire set of patients. This is significant in that it provides confidence that these precursor s-grams are, in fact, related to abnormalities.

After executing the program of instructions according to the methods described above, and as seen in FIGS. 1 and 2, the computer apparatus 10 can provide the output tables and graphs seen in FIGS. 3 through 8 on a visual display or through printed out reports.

This has been a description of examples of the invention. It will apparent to those of ordinary skill in the art that certain modifications might be made without departing from the scope of the invention, which is defined by the following claims.

We claim:

1. A method for processing data in medical records using a computing apparatus for determining a parameter of a health abnormality precursor, the method comprising:
    inputting documents into the computing apparatus representing a starting group of medical records having a minimum number of reports over a selected time interval;
    processing the starting group of medical records to generate respective document vectors;
    sampling the document vectors by applying a maximum variation sampling function to the document vectors;
    applying a fitness function to the results of the sampling, including factors to reduce a number of medical records to a reduced group of medical records and to increase the diversity of the medical records for further processing;

extracting linguistic phrases from the reduced group of medical records and converting the linguistic phrases to normal health and abnormal health s-grams;

applying a Haar wavelet function to the s-grams from medical records in the reduced group of medical records remaining after applying the fitness function;

further reducing the number of medical records in the reduced group of medical records for reporting by analyzing coefficient results from applying the Haar wavelet function according to at least one of a plurality of preselected s-gram patterns; and reporting abnormal health s-grams together with a parameter of a health abnormality precursor through a computing output device to a human observer.

2. The method of claim 1, wherein the s-grams represent medical conditions identified from a doctor; and wherein the parameter relating to the health abnormality is a percentage of occurrences of the medical condition which correlate to later development of the health abnormality as reported in the medical records being processed.

3. The method of claim 1, wherein the s-grams represent medical conditions identified from a doctor; and wherein the parameter relating to the health abnormality is a precursor lead time of the medical condition which later was recorded in the medical records being processed.

4. The method of claim 1, wherein the s-grams represent medical conditions identified from a doctor; and wherein the parameter relating to the health abnormality is a percentage of increase in occurrences of the medical condition which correlate to later development of the health abnormality reported in the medical records being processed in comparison with occurrences in a larger sampling of medical records for a larger group of medical, patients.

5. The method of claim 2, 3 or 4, wherein medical conditions are identified by a radiologist in medical reports created upon review of medical images produced by medical image modalities.

6. The method of claim 2, 3 or 4, wherein the parameter is reported within a table that is observed on a visual display.

7. The method of claim 1, wherein processing the starting group of medical records to generate respective document vectors includes removing punctuation marks and symbols; removing stop words; and parsing each medical record into a list of stemmed words.

8. The method of claim 1, wherein applying the fitness function to the results of the sampling includes making a computation according to the expression:

$$\text{Fitness}(i) = \sum_{j=0}^{N} \sum_{k=j+1}^{N} \alpha_j + \beta k + \text{Similarity}(vect(i, j), vect(i, k))$$

where i is an individual patient, and j and k are medical reports for patient i.

9. The method of claim 8, wherein $\alpha_j$ computed according to the function $$\alpha_j = e^{-\left(\frac{\|j\|}{100}\right)}$$

and wherein $\beta_k$ is computed according to the expression:

$$\beta_k = e^{-\left(\frac{\|k\|}{100}\right)}.$$

10. A computer program stored in a non-transitory medium for processing data in medical records using a computing apparatus for determining a parameter of a health abnormality precursor, the computer program comprising:

instructions for receiving documents into the computing apparatus representing a starting group of medical records dated within a preselected time interval;

instructions for processing the starting group of medical records to generate respective document vectors;

instructions for sampling the document vectors by applying a maximum variation sampling function to the document vectors;

instructions for applying a fitness function to the results of the sampling, including factors to reduce, a number of medical records to a reduced group of medical records and to increase the diversity of the medical records for further processing;

instructions for extracting linguistic phrases from the reduced group of medical records and converting the linguistic phrases to s-grams;

instructions for applying a Haar wavelet function to the s-grams from the reduced group of medical records over the preselected time interval;

instructions for further reducing the number of medical records for reporting by analyzing coefficient results from applying the Haar wavelet function according to at least one of a plurality of preselected s-gram patterns; and instructions for processing the reduced number of medical records and reporting abnormal health s-grams with a parameter representing a health abnormality precursor through a computing output device to a human observer.

11. The computer program of claim 10, wherein the s-grams represent medical conditions identified from a doctor; and wherein the parameter relating to the health abnormality is a percentage of occurrences of the medical condition which correlate to later development of the health abnormality as reported in the medical records being processed.

12. The computer program of claim 10, wherein the s-grams represent medical conditions identified from a doctor; and wherein the parameter relating to the health abnormality is a precursor lead time of the medical condition which later was recorded in the medical records being processed.

13. The computer program of claim 10, wherein the s-grams represent medical conditions identified from a doctor; and wherein the parameter relating to the health abnormality is a percentage of increase in occurrences of the medical condition which correlate to later development of the health abnormality reported in the medical records being processed in comparison with occurrences in a larger sampling of medical records for a larger group of medical patients.

14. The computer program of claim 11, 12 or 13, wherein medical conditions are identified by a radiologist in medical reports created upon review of medical images produced by medical image modalities.

15. The computer program of claim 11, 12 or 13, wherein the parameter is reported within a table that is observed on a visual display.

16. The computer program of claim 10, wherein processing the starting group of medical records to generate respective document vectors includes removing punctuation marks and symbols; removing stop words; and parsing each medical record into a list of stemmed words.

17. The computer program of claim 10, wherein applying the fitness function to the results of the sampling includes making a computation according to the expression:

$$\text{Fitness}(i) = \sum_{j=0}^{N} \sum_{k=j+1}^{N} \alpha_j + \beta_k + \text{Similarity}(vect(i,j), vect(i,k))$$

where i is an individual patient, and j and k are medical reports for patient i.

18. The computer program of claim 17, wherein $\alpha_j$ is computed according to the function $$\alpha_j = e^{-\left(\frac{\|j\|}{100}\right)}$$

and wherein $\beta_k$ is computed according to the expression:

$$\beta_k = e^{-\left(\frac{\|k\|}{100}\right)}.$$

\* \* \* \* \*